US005681329A

United States Patent [19]
Callicrate

[11] Patent Number: 5,681,329
[45] Date of Patent: Oct. 28, 1997

[54] METHOD AND APPARATUS FOR CASTRATION USING AN ENDLESS ELASTIC LOOP

[76] Inventor: Michael P. Callicrate, P.O. Box 602, St. Francis, Kans. 67756

[21] Appl. No.: 414,638

[22] Filed: Apr. 3, 1995

Related U.S. Application Data

[63] Continuation-in-part of Ser. No. 86,806, Jul. 2, 1993, Pat. No. 5,403,325, which is a continuation-in-part of Ser. No. 807,727, Dec. 16, 1991, Pat. No. 5,236,434.

[51] Int. Cl.⁶ .................................................. A61B 17/00
[52] U.S. Cl. ......................... 606/141; 606/135; 606/139; 606/151; 606/203
[58] Field of Search .............................. 606/135, 139, 606/140, 141, 203, 163, 165, 151, 157, 158, 110–113, 228, 232, 201; 124/17, 20.1; 24/17 B

[56] References Cited

U.S. PATENT DOCUMENTS

| | | |
|---|---|---|
| 612,569 | 10/1898 | Moscrop . |
| 1,615,125 | 1/1927 | Lespinasse ............... 606/135 |
| 1,885,945 | 11/1932 | Ransy . |
| 2,125,404 | 8/1938 | Snyder ..................... 606/140 |
| 2,487,425 | 11/1949 | Collins . |
| 2,642,057 | 6/1953 | Watkins .................... 124/17 |
| 3,080,867 | 3/1963 | Eichinger ................. 606/113 |
| 3,547,124 | 12/1970 | Fergusson . |
| 3,687,138 | 8/1972 | Jarvik . |
| 3,726,278 | 4/1973 | Scott . |
| 3,813,983 | 6/1974 | Paul ........................ 81/469 |
| 3,983,860 | 10/1976 | Bolton ..................... 124/20.01 |
| 4,220,155 | 9/1980 | Kimberling et al. . |
| 4,335,490 | 6/1982 | Teachout .................. 24/17 B |
| 4,569,324 | 2/1986 | Garcia ..................... 124/20.01 |
| 4,572,179 | 2/1986 | Tietelbaum et al. . |
| 4,682,716 | 7/1987 | Morellini . |
| 4,691,704 | 9/1987 | Wadsworth . |
| 4,721,169 | 1/1988 | Nagasawa et al. ........ 81/469 |
| 4,966,057 | 10/1990 | Koppatsch ................ 81/469 |
| 4,966,600 | 10/1990 | Songer et al. ............ 606/74 |
| 4,986,369 | 1/1991 | Fushiya et al. ........... 81/467 |
| 5,127,389 | 7/1992 | Magnuson ................ 124/20.01 |
| 5,163,948 | 11/1992 | Kummer .................. 606/151 |
| 5,188,637 | 2/1993 | Wadsworth ............... 606/151 |
| 5,279,276 | 1/1994 | Nagel et al. .............. 124/20.1 |
| 5,282,825 | 2/1994 | Muck et al. .............. 606/203 |
| 5,459,905 | 10/1995 | Voyre ....................... 24/17 B |
| 5,520,702 | 5/1996 | Sauer et al. .............. 606/148 |

FOREIGN PATENT DOCUMENTS 1201722  9/1965  Germany ................. 124/20.1

*Primary Examiner*—Jeffrey A. Schmidt
*Attorney, Agent, or Firm*—Sheridan Ross P.C.

[57] ABSTRACT

A method and apparatus (10) for applying a preformed endless band (18) of elastomeric ligature material to an animal body part is provided, such method employing a motor to facilitate the winding of ligature material. The apparatus (10) includes a winding assembly (14) for winding the band (18), wherein a loop (20) of the band (18) is tightened by winding the band (18). A crimping assembly (16) for crimping a grommet (32) to secure the loop (20) is also disclosed. The invention allows the loop (20) to be quickly and tightly secured using pneumatic/electric tools or motors.

32 Claims, 11 Drawing Sheets

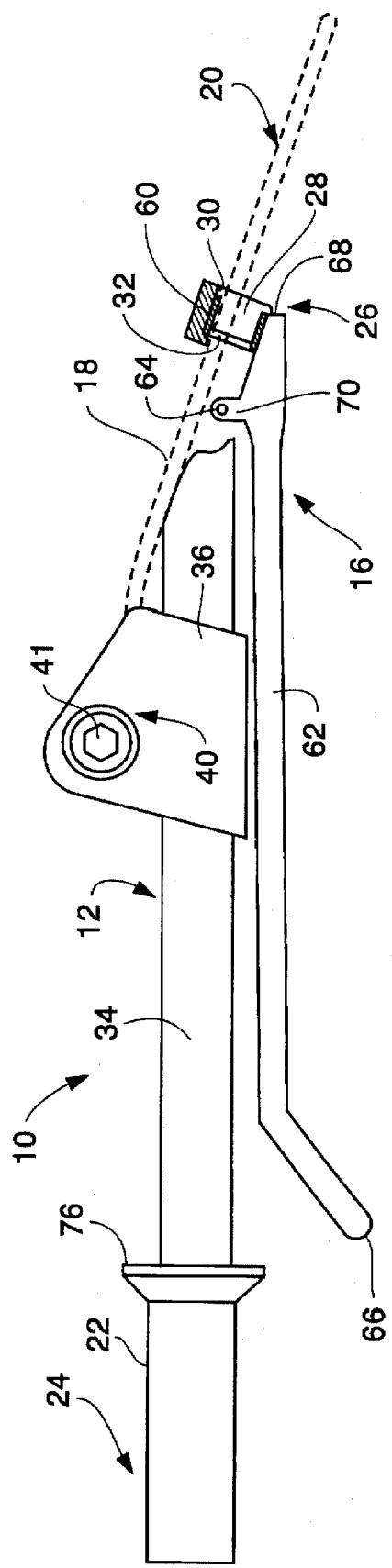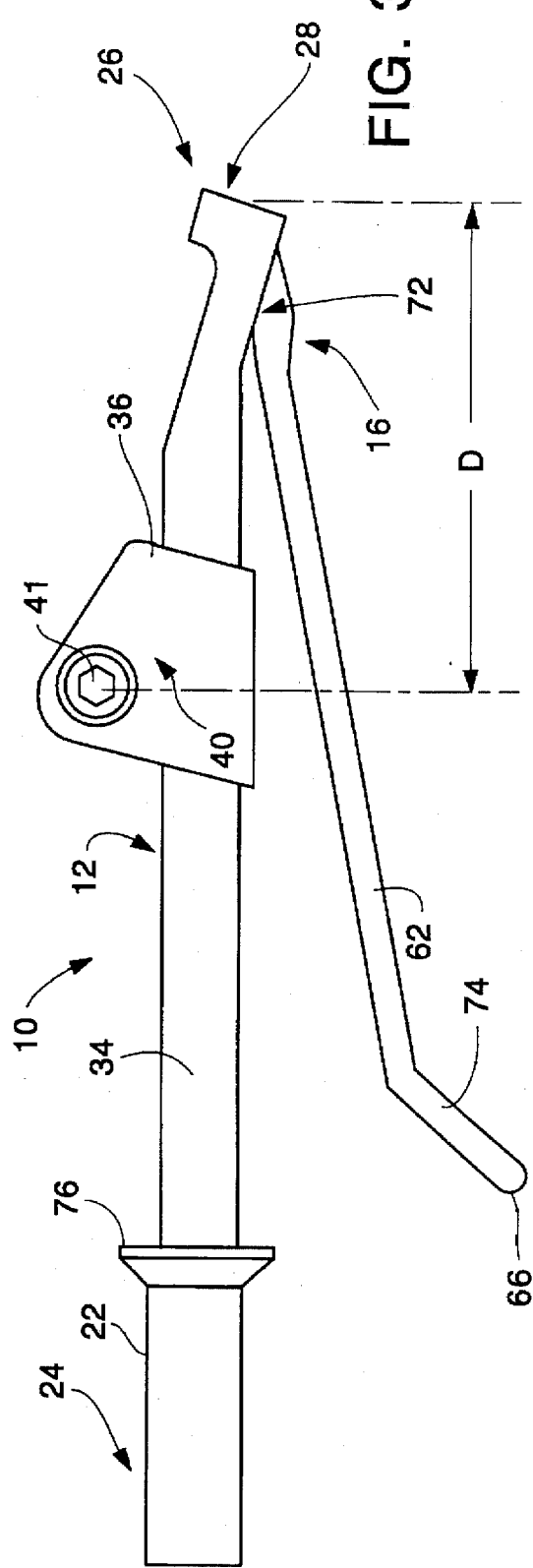

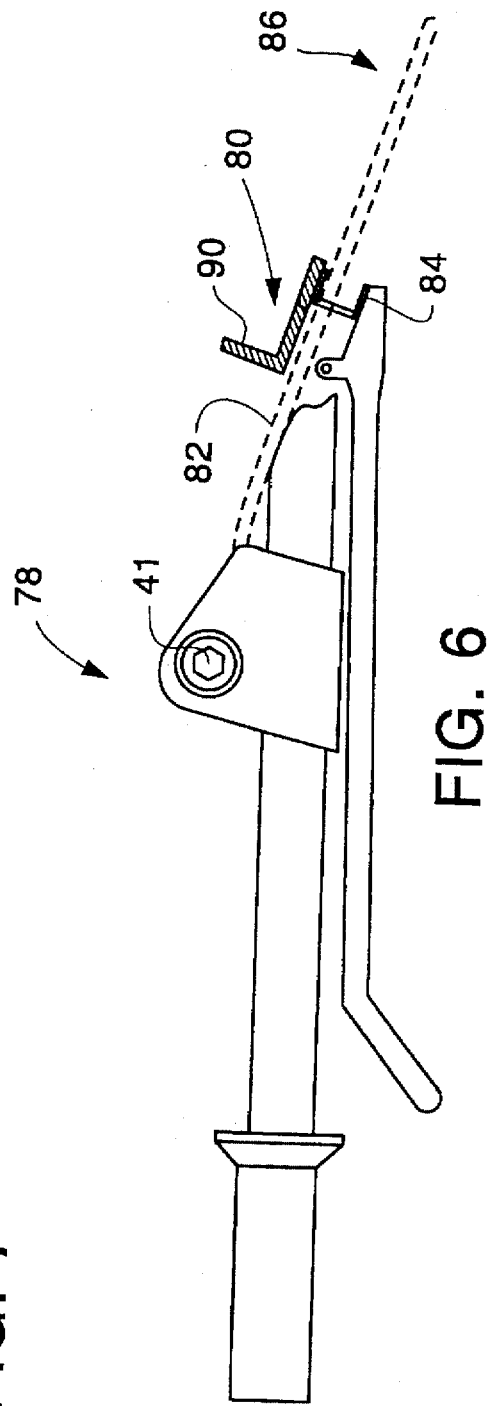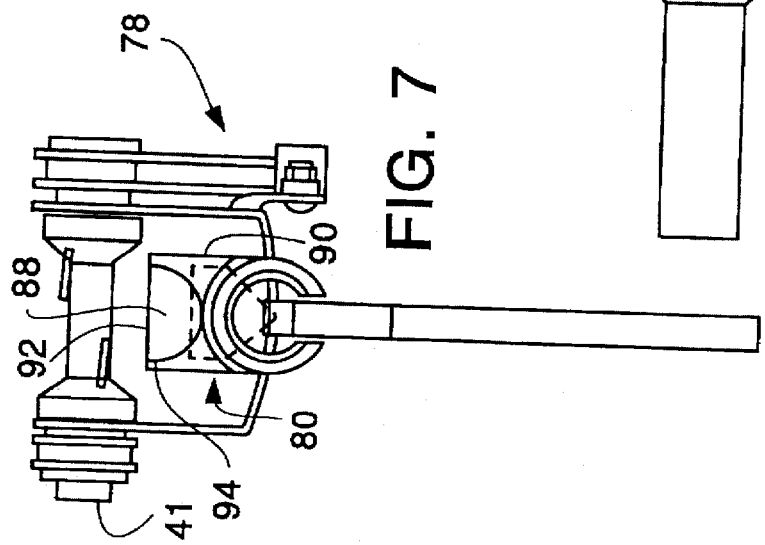

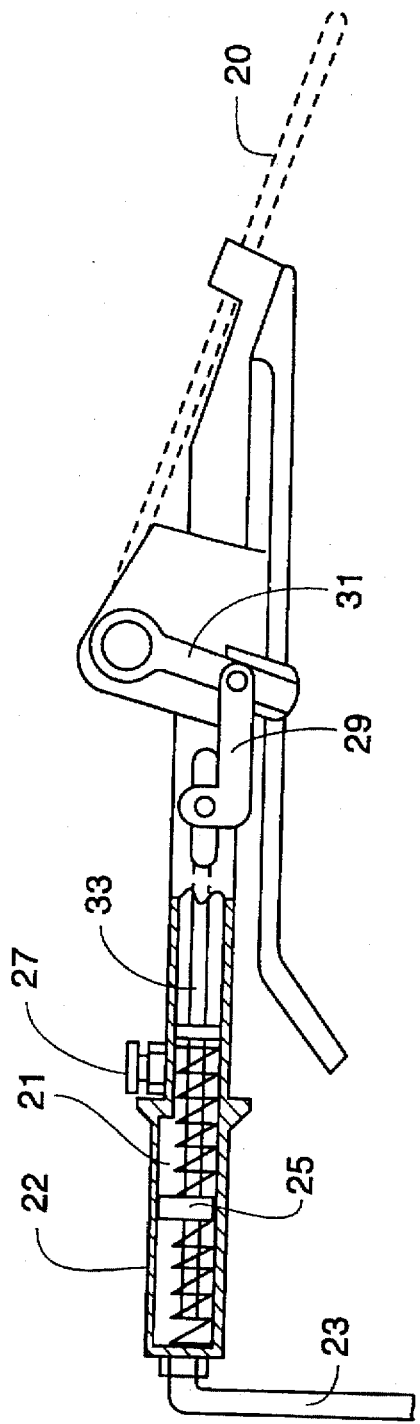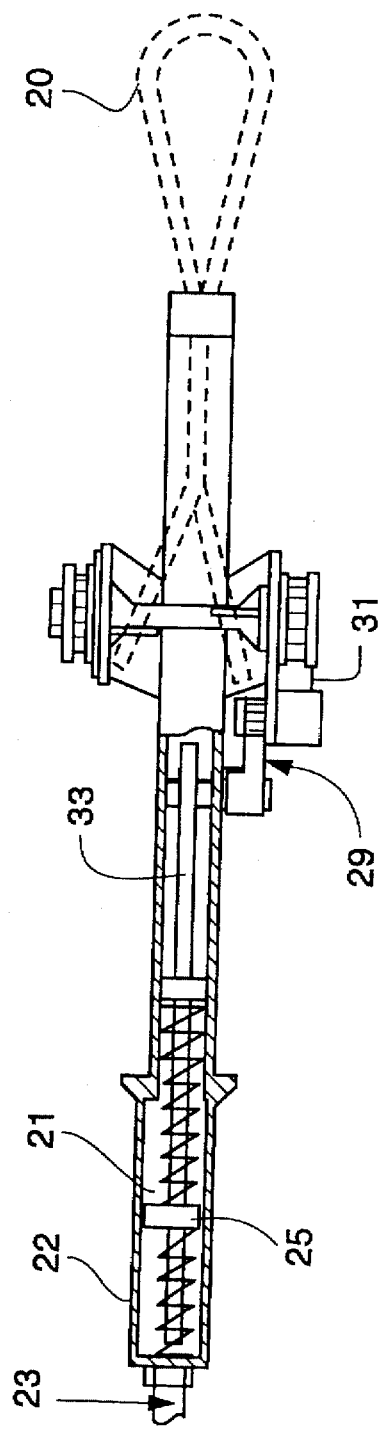
Fig. 8
Fig. 9

1

METHOD AND APPARATUS FOR CASTRATION USING AN ENDLESS ELASTIC LOOP

RELATED APPLICATION

The present application is a continuation-in-part application of U.S. patent application Ser. No. 08/086,806 filed Jul. 2, 1993 now U.S. Pat. No. 5,403,325 and entitled POWER LIGATION TOOL AND METHOD which was a continuation-in-part application of U.S. patent application Ser. No. 07/807,727, filed Dec. 16, 1991 now U.S. Pat. No. 5,236,434 and entitled "METHOD AND APPARATUS FOR LIGATING A BODY PART" by Callicrate. These related applications are incorporated herein by reference in their entirety.

FIELD OF THE INVENTION

This invention relates in general to ligature tools and in particular to a method and apparatus for applying a ligature band to an animal body part. This invention further relates to a method and apparatus for applying a preformed endless ligature loop to an animal's scrotum, including means for deforming a grommet to secure the endless loop.

BACKGROUND OF THE INVENTION

A common method for the removal of a body part is ligation. Ligation is a process in which a band or cord is fastened to the body part to be removed in order to constrict it, thus cutting off the supply of blood and systemic support. The body part thereafter atrophies and drops away from the body. Ligation has been used for many purposes including castration and the removal of horns, tails or other body parts from animals.

Ligation has a number of advantages over surgical procedures for such applications. First, ligation has a safety advantage in that the animal normally does not become susceptible to infection. For example, in the case of castration of bulls, a period of about two weeks to a month typically passes between the time that the ligature is attached to the scrotum and the time that the scrotum drops off. During this time the area adjacent the ligature heals, thus reducing the likelihood of infection. Another advantage of ligation is that ligation can be performed quickly by non-expert personnel, thereby reducing costs. In addition, when the ligature is sufficiently tight, ligation can generally be performed with little stress on the animal because the body part numbs quickly after the blood supply is cut off.

According to one conventional method of ligation, an endless loop of elastic band is stretched to encircle a body part and is used to cut off the blood supply to the body part to be removed. Because the band is endless, the band must be stretched to open it up a sufficient amount so that it can be positioned by passing the band loop over the body part as disclosed in U.S. Pat. No. 4,527,179. This conventional method has the disadvantage that it is difficult to attach the ligature band such that it is sufficiently tight. For example, when an endless band is used to castrate bulls, the band must be stretched to pass over the scrotal sac and its contents and then released to engage the sac at the desired position. The tightness of the band when positioned is therefore limited by the band's elasticity. In addition, because an endless ligature band generally cannot be tightened, the size of the band loop can only be roughly matched to a particular application. That is, the band is usually selected from a limited number of discrete band sizes. Because of the difficulty in tightening conventional endless bands, such bands may fail to sufficiently cut off the blood supply resulting in prolonged stress to the animal and an increased likelihood of swelling and/or infection. In addition, there is a greater chance that the animal will intentionally or unintentionally displace a loose band.

Another ligation method is disclosed in U.S. Pat. No. 4,691,704. A loop of a ligature elastomeric band is formed around the body part to be ligated, and then an end portion of the band is attached to a tightening rod. The tightening rod can then be retracted in a substantially linear fashion by successive pulls on a trigger mechanism, thereby tightening the loop. However, the process of tightening the loop through successive pulls on the trigger mechanism is time consuming and the animal must therefore be restrained for a longer period of time. In addition, the tension which can be imparted to the band, and the tightness of the loop, are limited by the hand strength of the user. Moreover, relatively large frictional and abrasive forces are exerted on the band where the band is attached to the tightening rod, thereby increasing the likelihood of damage to the elastomeric material causing breakage before the desired tension is achieved. Furthermore, the attachment of the end portions of the band can be time consuming and thus impede the speed at which cattle or other livestock can be processed. Additionally, due to the design of the ligature tool, an operator is limited in the extent a band can be tightened. Once an operator has fully retracted the tightening rod, the loop's tightness cannot be increased.

The inability to achieve relatively quick and complete occlusion of both venous and arterial pressure within the body part being ligated may result in the venous pressure alone being shut off, thereby permitting the stronger arterial pressure to fill the body part with blood. This, in turn, can lead to swelling of the body part and failure of the ligation process, causing consequential pain to the animal.

SUMMARY OF THE INVENTION

The present invention discloses a method and apparatus for ligation which avoids or alleviates the problems discussed above. The present invention allows a ligature band to be tightly attached to an animal body part thereby reducing the likelihood of swelling, infection and/or prolonged stress to the animal. The present invention also allows the band to be tightened quickly thereby reducing the length of time that the animal must be restrained.

According to the present invention, a method and apparatus for ligation is provided. The method includes the steps of forming a loop about the body part with a band of ligature material and winding the band to tighten the loop. Preferably, the band is tightened by securing the band to a spool and then rotating the spool to wind the band. After the loop is tightened, the loop can be secured by crimping a grommet so that the band is secured therein.

A separate aspect of the present invention relates to a method and apparatus for using a preformed endless loop to sever animal parts. Use of an endless ligation loop eliminates the conventional practice of using a linear length of banding material to form a loop around a body part and avoids the subsequent need to attach the respective ends of the band to a means for pulling the band to tighten the loop. Furthermore, use of a pre-formed loop (i.e., formed prior to insertion of any band material into a ligation device) eliminates the need for cumbersome lengths of ligation material used in conventional ligation operations and enables an operator to slip pre-formed loops over his/her arms or legs, thus facilitating easy access to such loops when performing multiple ligation procedures. Moreover, use of pre-formed loops having pre-attached grommets ensures that a loop is never tightened without a grommet first being in place. The likelihood of losing the grommet is also reduced and the preformed endless loop may be inserted in the tool and attached to a means for pulling in a more efficient manner. The pre-formed loop having a grommet pre-attached to the loop, (preferably to form an hour-glass shaped loop) is useful not only with the winding tool disclosed herein, but is also useful with prior art devices, such as the "caulking gun-type" device described by Wadsworth, U.S. Pat. No. 4,691,704.

A tool constructed in accordance with an embodiment of the present invention includes a receiving device for receiving a band of ligature material, wherein the band forms a loop external to the receiving device. A winding assembly is interconnected to the receiving device such that the loop is tightened by winding the band.

Preferably, the winding assembly includes a spool that facilitates the securing of a band thereabout as the spool is rotated. A ratchet mechanism can be employed to provide for one way rotation of the spool. In a preferred embodiment, the tool is operated by pneumatic or electrical motors or by power tools which function to wind the band around the spool to achieve a desired loop tightness or tension. More preferably, the motor or power source used to wind the tool is recessed within the handle portion of the tool and engages a worm gear or other similar mechanism to rotate the winding spool. The tightness of the loop can be modified by adjusting either the pneumatic/electrical winding device so that winding of ligature material ceases at a predetermined tension, or by providing a clutch mechanism on the tool itself. The winding assembly may rotate in a direction perpendicular to the longitudinal axis of the tool effectively shortening the endless loop and applying pressure around the selected body part of the animal.

In a preferred embodiment, the tool includes a lever which is biased against the grommet located in a receptacle in the receiving end of the tool. The pressure exerted by the lever prevents the grommet from inadvertently being mispositioned prior to and during the operation of the tool. Furthermore, when sufficient tension is put on the endless loop and consequent pressure is applied to the body part to be severed, the lever is used to deform the grommet upon and/or around the endless loop to secure the loop around the animal's body part. When it is desired to release the tool from the ligature material, the lever position is reversed.

BRIEF DESCRIPTION OF THE DRAWINGS

FIG. 2 is a side view, partially cut away, of the apparatus of FIG. 1;

FIG. 3 is a side elevational view of the apparatus of FIG. 1 with the crimping arm in a deflected position;

FIG. 6 is a side view, partially cut away, of an apparatus constructed in accordance with the present invention showing a cutting assembly;

FIG. 7 is a front view of the apparatus of FIG. 6; and

FIG. 8 is a side partial section elevational view of one embodiment of the present invention in which a power winding source is integral with the ligation tool itself.

FIG. 9 is a top partial section view of one embodiment of the present invention in which a power winding source is integral with the ligation tool itself.

DETAILED DESCRIPTION OF THE INVENTION

Figure 1:
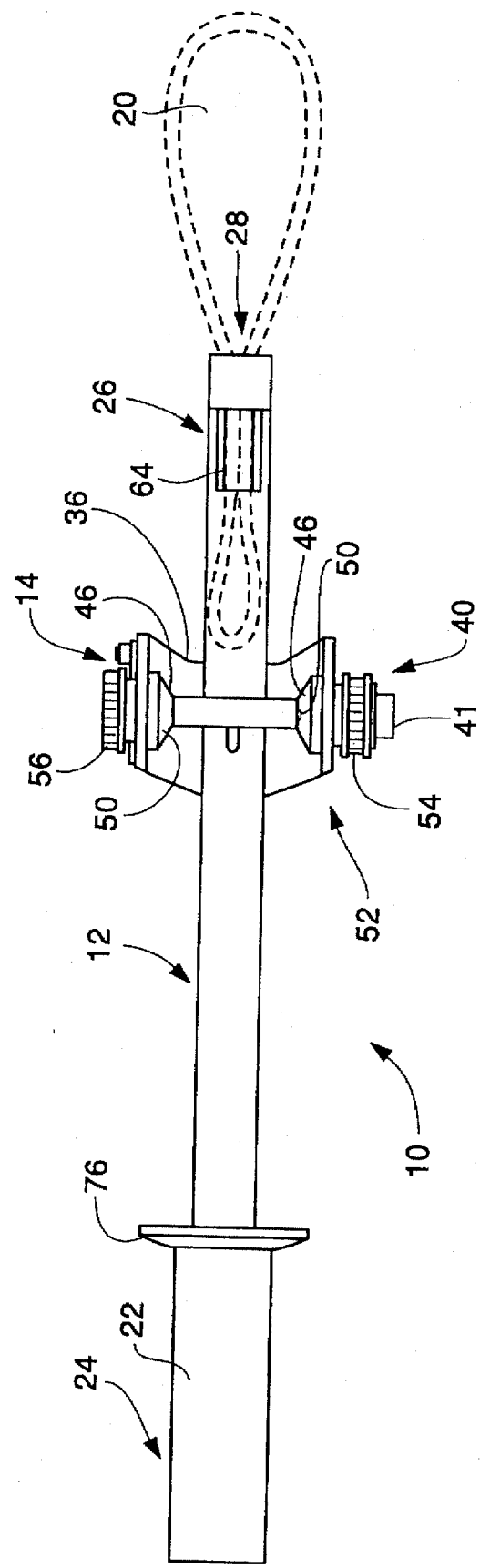
FIG. 1 is a top view of an apparatus constructed in accordance with the present invention.
Figure 4:
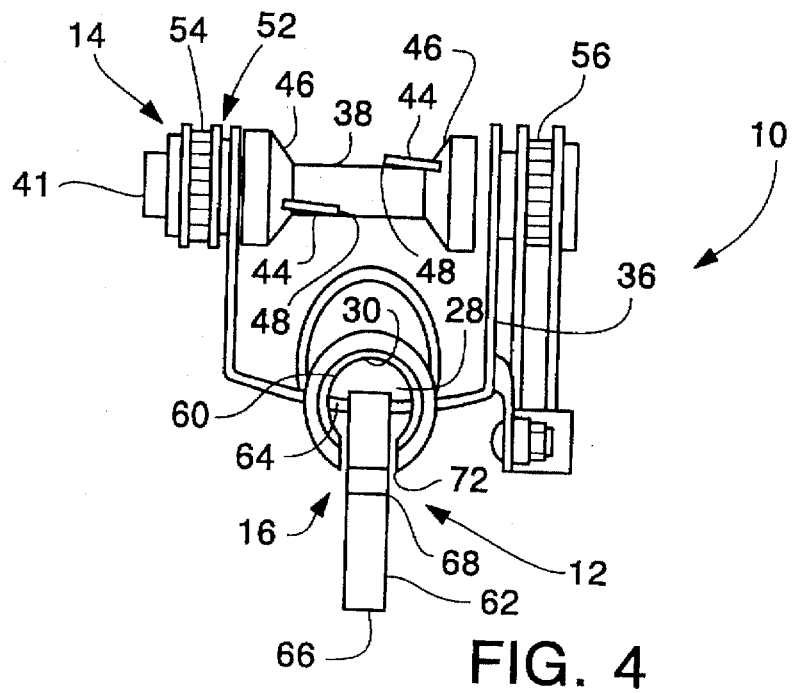
FIG. 4 is a front elevational view of the apparatus of FIG. 1.

Referring to FIGS. 1–4, an apparatus constructed in accordance with an embodiment of the present invention is generally identified by the reference numeral 10. As shown, the apparatus 10 comprises a tool body 12, a winding assembly 14 and a crimping assembly 16.

The body 12 receives a band 18 of ligature material, wherein a loop 20 of ligature material is formed external to the apparatus 10 about an animal body part to be removed. The loop 20 is then progressively tightened by winding the band 18 about winding assembly 14 to substantially cut off blood flow and systemic support to the animal body part. Preferably, the ligature material comprises an elastomeric material such as surgical tubing. However, because of the large tightening forces which can be achieved with the apparatus 10, relatively inelastic band materials such as rope and/or wire may be successfully employed.

The tool body 12, which may comprise steel or other material having sufficient strength to withstand the forces encountered during ligation procedures, has a handle 22 at a first end portion 24 thereof and a second end portion 26 which is adapted to receive the band 18 of ligature material. The handle 22 may be contoured for optimal handling by the user. In the illustrated embodiment, the second end portion 26 includes a passageway 28 sufficient to allow passage of the band 18 therethrough. The second end portion 26 can also include a receptacle 30 adapted to hold a grommet 32 which can be crimped, as will be described below, to secure the band 18 after the loop 20 has been tightened. It will be appreciated that the band 18 of ligature material is pulled rearwardly through the passageway 28 towards the winding assembly 14 as the loop 20 is tightened. As illustrated, the second end portion 26 may be angled relative to a longitudinal portion 34 of the body 12, the angle preferably selected such that a longitudinal direction of the second end portion 26 is directed towards the winding assembly 14, thereby reducing frictional and binding contact between the band 18 and the second end portion 26 as the band 18 is pulled therethrough. Reducing such frictional and binding contact facilitates winding of the band 18 by reducing the effort which must be exerted by the user in winding and reducing the likelihood that the band 18 will become snagged and possibly break.

The winding assembly 14 is attached to the body 12 by way of frame 36 which may comprise steel or other material of suitable strength. Frame 36 provides a distance x between the body 12 and the winding assembly 14 which is sufficient to substantially prevent mechanical interference between the band 18 and the body 12 as the band 18 is wound about the assembly 14. Preferably, the distance x is between about ¼ inch and two inches depending, for example, on the thickness of the band 18 employed. In the illustrated embodiment, the distance x is about ½ inch which has been found to provide sufficient clearance for a broad range of materials, including standard surgical tubings.

In one embodiment of the present invention, the winding assembly 14 comprises a spool 38 which is rotatably mounted on the frame 36 and a winding engagement site 41 operatively connected to the spool 38 is provided which can be rotated by a pneumatic or electrical power motor 43, such motor being integral to or alternatively separate from the frame 36. The power tool 45 or motor 43 utilized must be capable of engaging the winding engagement site 41 in a manner so that the winding means 14 is turned or rotated, thus facilitating the accumulation of ligature material on the winding assembly 14. In one embodiment, the winding engagement site 41 comprises a suitably designed protuberance, such as a nut having several sides, or an indentation, similarly having a plurality of sides, engagable by a suitably complementary power tool 45 device that is capable of activating the winding means 14 to achieve rotation thereof. The compatible multi-sided protuberance or multi-sided indentation is configured so that engagement of the power tool 45 or motor device 43 with such protuberance or indentation will facilitate the powered rotation of the winding means 14.

In another embodiment, the powered winding of ligature material is achieved by the incorporation of a pneumatic or electrical device into the tool's 10 overall design so that a separate power tool 45 need not be interconnected or engaged with a separate powered tool. As such, the incorporation of a pneumatic or electrical powered motor 43 that is integral with the castration tool 10 is within the scope of the present invention. An illustrative embodiment of such embodiment is shown in FIGS. 8 and 9.

With reference to FIGS. 8 and 9, a pneumatic device 21 is incorporated into the handle 22 of the tool 10. An air supply 23 can be interconnected with one end of the handle 22 to operate an air piston 25 residing within the handle 22. An air control valve 27 located on the handle 22 can be used to control the winding operation so as to achieve desired winding of ligature material about the spool 38. In one embodiment, a drive linkage 29 between the pneumatic device 21 and the winding assembly 14 is provided to permit operation of a ratcheted lever 31 having an axis of rotation coincident with the axis of rotation of the spool 38. The lever 31 is attached to a ratchet mechanism 52 so that the spool 38 can be selectively rotated in alternative directions. The drive linkage 29 is operatively attached to a piston rod 33 which is driven by the air piston 25 located in the tool's handle 22. Upon operation of the air piston 25, the piston rod 33 is moved back and forth within the body 12 of the device. Through such movement the drive linkage 29 communicates with the ratcheted lever 31 to rotate the spool 38 in a desired direction. Winding of the ligature material 20 around the spool 38 can thus be accomplished by regulating the number of times the air piston 25 is forced forward and backwards, thereby ratcheting the ligature material 20 around the spool 38 to achieve a desired tension of the ligature loop 20. In another embodiment, an electric or pneumatic motor is incorporated into the handle 22 of the tool 10 and is interconnected to a worm gear or other type of gearing mechanism. The worm gear is then operatively positioned to another gear interconnected to the winding spool 38. As can be appreciated by one skilled in the art, numerous types of gearing configurations may be implemented to transfer power from the motor to the winding spool 38.

In some applications, it is important to regulate the tightness or tension of a ligature loop 20 to prevent breakage thereof or to prevent injury to the animal. The tightness of ligature material can be regulated by adjusting the amount of force communicated by the rotation of the winding means 14 by a motor 43. This can be accomplished by, for example, a clutch mechanism 47 either incorporated into the winding means 14 or, alternatively, can be a feature of the power tool 45. For instance, a pneumatic power tool 45 capable of rotating the winding means 14 can be adjusted so that no further rotations occur after a predetermined tension or torque is achieved, at which point air is bled from the pneumatic power tool 45 rather than being used to rotate the winding assembly 14. The ligature material is therefore wound about the winding means 14 to a pre-determined tension, such tension regulated by a clutch mechanism 47 operatively associated with the motor 43 or in alternative embodiments, a feature of the power tool 45.

As can be readily appreciated, the rate at which the loop 20 is tightened will depend upon the diameter of the spool 38 and the speed of rotation of the spool 38. In addition, the tension which can be imparted to the band 18 by winding the band a predetermined number of times around the spool 38 or, alternatively, by gauging the tension or torque exerted on the winding assembly 14 so that at a predetermined desired tension, the spool 38 is no longer rotated. The diameter of the spool 38 can therefore be selected to allow the desired rate and degree of tightening. Although it is believed that a broad range of spool 38 diameters would provide adequate results, the illustrated spool 38 has a diameter between about ½ inch and ¾ inch. Such a diameter allows for rapid tightening of the loop 20 and allows the loop 20 to be sufficiently tightened to substantially cut off blood flow and systemic support to the body part to be removed.

The spool 38 further includes fasteners 44 to attach the band 18 to the spool 38. The fasteners 44 may comprise a slotted portion of the spool 38, a clip biased against the spool 38 or any other device by which the band 18 can be secured to the spool 38. Where an elastomeric band is employed, is it expedient to provide a fixed element closely adjacent to a surface of the spool 38 so that the band 18 can be frictionally secured therebetween. In the illustrated embodiment, the fasteners 44 comprise cantilevered rods extending inwardly from flanged end portions 46 of the spool 38. The fasteners 44 can be positioned such that the space between the spool 38 and a fastener 44 is progressively restricted from a free end 48 to a base 50 of the fastener 44. Such a configuration allows the band 18 to be quickly and reversibly secured to the spool 38 by inserting the band 18 between the spool 38 and the free end 48 and then sliding the band 18 towards the base 50 until the band 18 is securely wedged therein.

The winding engagement site 41 is interconnected to the spool 38 such that the spool 38 can be rotated by turning of the winding means 14. A ratchet assembly 52 can be employed to facilitate rapid tightening of the loop 20. The assembly 52 comprises a first ratchet and pawl mechanism 54 which cooperates with a second ratchet and pawl mechanism 56 at the opposite end of the spool 38 to allow rotation of the spool 38 in only one direction. The user can thus tighten the loop 20 through repeated turnings of the spool 38 and the pneumatic or electric winding device 43 can be adjusted so that at a desired tension, no further winding of the spool 38 occurs. The present invention therefore provides a method and device that facilitates the speedy ligation of animal parts, and thus considerably shortens the time period required to perform the ligation procedure. This spares the user from exposing himself/herself to extended periods of danger encountered when working with large animals and lessens the discomfort of the animals.

Although particular dimensions for the illustrated embodiment have been provided, it is within the scope of the present invention to have a tool body of any dimensions, thus allowing for variation of the distance between the operator and animal.

Although not shown, it will be appreciated that the ratchet assembly 52 could be eliminated and the winding engagement site 41 could instead be rigidly interconnected to the spool 38 with appropriate modification of the apparatus 10. It will be further appreciated that a winding engagement site 41 can be positioned on either or both sides of the body 12 to facilitate right hand or left hand users.

After the loop 20 has been tightened, the loop size can be maintained by securely interconnecting portions of the band 18 adjacent the loop 20. The portions may be interconnected by using an adhesive; stapling, pinning or heat sealing the band 18; binding portions of the band with wire, rope or the like; or any other suitable method for securing the loop 20. In the illustrated embodiment, a crimping assembly 16 is provided to crimp a grommet 32 after the loop 20 has been tightened, thereby securing the loop 20. The grommet 32 preferably comprises a cylindrical structure having an interior passageway sufficient to allow passage of the band 18 therethrough and can be formed from aluminum or other deformable material. During the ligation procedure, the grommet 32 is housed within a receptacle 30 of the second end portion 26. As shown most clearly in FIG. 4, the receptacle 30 can include an internal annular shoulder 60 such that the grommet 32 can be positioned by sliding the grommet 32 into the receptacle 30 until an end of the grommet 32 abuts the shoulder 60.

The grommet 32 used with the present invention can be of any desired shape and dimension to fit appropriately in the receptacle 30. The grommet 32 must be capable of being properly crimped in a manner sufficient to hold two bands 82 together so as to form a loop 20 of ligature material. The grommet 32 must retain the loop 20 in a tensive condition during the atrophy process which may take several weeks. Further, the grommet 32 is designed so as to securely fasten the ligature material without significantly damaging the material. The grommet 32 can be a completely enclosing angular structure or may alternatively be configured with side portions bendable to secure each individual end of the ligature material, thus independently fastening each end without being dependent upon the adjacency of the other end to achieve a secure loop 20. The grommet 32 may further include indexing means comprising indentations or protuberances so that the grommet 32 is properly oriented within the tool 10 to achieve a desired crimping configuration.

Figure 5:
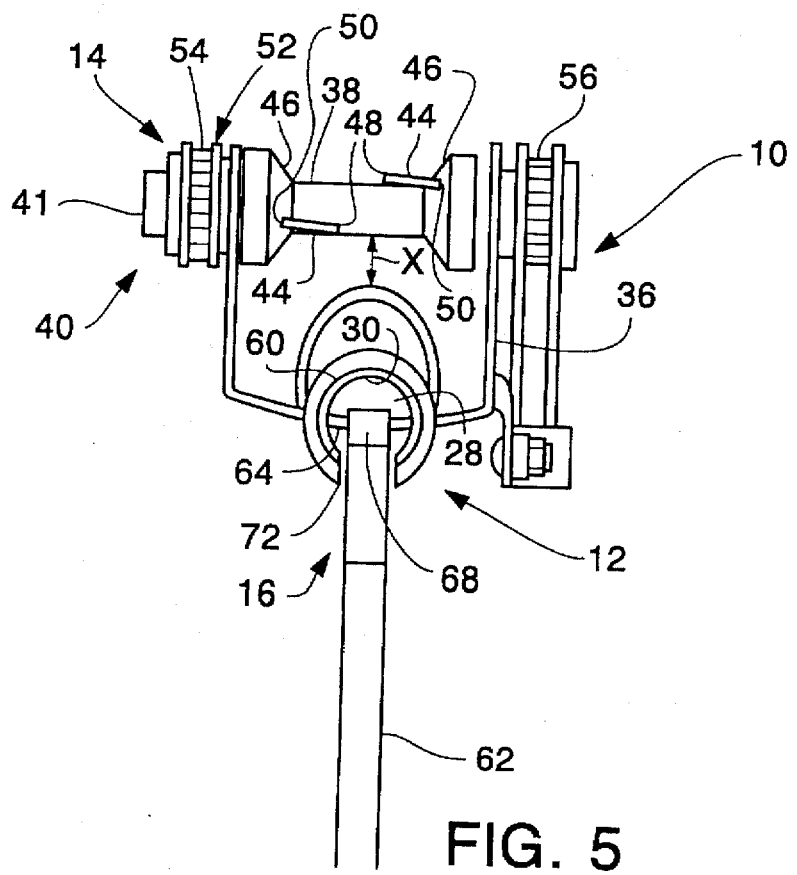
FIG. 5 is a front elevational view of the apparatus of FIG. 1 with the crimping arm in a deflected position.

The crimping assembly 16 comprises a lever 62 which is pivotally mounted on the body 12 by way of a fulcrum 64 such as a pin. The user can move the lever 62 from a retracted position (FIG. 3) to an extended position (FIGS. 4 and 5) by urging the rearward end 66 of the lever 62 downwardly as viewed in the figures. In the extended position, the forward end 68 of the lever 62 extends into the receptacle 30 to deform the grommet 32. As shown, the fulcrum 64 is preferably positioned towards the forward end 68 of the lever 62 so that a relatively small downward force exerted on the rearward end 66 of the lever 62 by the user results in a greater crimping force on the grommet 32.

The fulcrum 64 penetrates a bulge portion 70 of the lever 62 which extends through a slot 72 in the body 12. Forwardly from the fulcrum 64, the lever 62 tapers so that the lever 62 can be fully withdrawn from the receptacle 30 in the retracted position. In addition, the illustrated lever 62 includes a downwardly extending portion 74 adjacent the rearward end 66 of the lever 62 to avoid mechanical interference with a flange 76 of the handle 22 and to provide sufficient clearance between the body 12 and the lever 62 for gripping by the user. If desired, the lever 62 may be contoured for optimal handling by the user or a grip (not shown) may be interconnected with the lever 62 for this purpose.

Referring to FIGS. 6 and 7, side and front views, respectively, of an apparatus 78 constructed in accordance with the present invention are shown. The apparatus 78 includes a cutting assembly 80 for cutting the band 82 rearwardly of the grommet 84 after the loop 20 has been tightened. Any device for cutting the band 82 may be employed in accordance with the present invention. For example, a hand-held razor, scissors or other cutting tool 10 may be employed. In the illustrated embodiment, the assembly 80 comprises a razor 88 slidably mounted within a housing 90 which is interconnected to or integral with the apparatus body or frame. Preferably, the cutting assembly 80 severs the band 82 a suitable distance rearwardly of the grommet 84 to reduce the likelihood that the band 82 will be pulled through the grommet 84 after severing. In this regard, it will be appreciated that elastomeric bands tend to constrict under tension and expand after severing such that such bands may slide a distance through the grommet 84 before becoming secured therein.

The razor is slidable from a retracted position, wherein the cutting surface of the razor 88 is protectively housed within housing 90, to an extended position (as shown in phantom in FIG. 7) wherein the cutting surface of the razor 88 extends into the band passageway to cut the band 82. The razor 88 can be moved from the retracted position to the extended position by pressing downwardly on an upper surface 92 of the razor 88, such that the upper surface 92 is urged downwardly through finger cut-out 94. Preferably, the razor 88 is biased upwardly, e.g. by a spring, so that the razor 88 remains in the retracted position until the razor 88 is pressed downwardly.

In operation, a tool 10 may be employed in accordance with the present invention to ligate a body part as follows. Initially, a band of ligature material is either looped around the body part and inserted through an end portion of the tool 10 and a grommet 32 housed therein, or a loop 20 is preformed and then positioned around the body part to be ligated. End portions of the band can then be attached to a spool by sliding the end portions between fasteners and the spool such that the end portions are frictionally engaged therebetween. Although not shown in the illustrated embodiments above, it will be appreciated that it would be sufficient to attach only one end portion of the band to the spool. For example, one end portion of the band could be connected to the spool and a second end portion could be connected to the body. In this regard, attaching the band to the spool at two end portions has the advantage that the band can be tightened quickly and evenly. However, attaching the band to the spool at only one end portion and allowing the other end portion to remain stationary as the band is tightened has the advantage that the stationary end portion need not be severed from a supply of band material prior to winding the band.

After the band is secured to the spool, the band can be tightened by turning or rotating the winding means 14. The band can be tightened by operation of a pneumatic or electrical winding tool 10 that engages the winding assembly 14 to thereby cause the spool to rotate, tightening the ligature loop 20. The present invention therefore provides a method and device for tightening a loop 20 around a body part without expenditure of physical strength, such as a user's hand strength. The tightness of the loop 20 is therefore not limited by the user's hand strength, allowing for the expedited ligation of body parts.

When the loop 20 is tightened sufficiently, the loop 20 can be secured by moving a crimping lever to an extended position thereby deforming the grommet 32 so that the band portions therein are frictionally secured. Thereafter, the band may be severed with a cutting tool 10, e.g., a razor, rearwardly of the grommet 32 leaving the loop 20 attached to the body part.

Another aspect of the present invention involves an endless elastomeric ligature loop 100 used for ligation of body parts, and particularly for castration. The prior art discloses the manual formation of an endless loop around a body part of an animal utilizing two ends from a substantially linear band of ligature material. The ends of the ligature bands are then attached to a means for pulling one or both of the ends of the ligation material to tighten the manually formed loop around the body part. In contrast, the present invention provides a preformed endless loop that is easy to attach to a tool for winding or pulling, and subsequently decreases material costs due to the absence of any excess length of ligature material used in securing such material to the ligation tool. The use of preformed endless loops of material, particularly loops having a pre-attached grommet thereon, reduces the time required to apply the endless ligature loop around the body part of a restrained animal. In a preferred embodiment, the endless loop is manufactured from an elastomeric material having resistant to e strength that is resistant to abrasion and tearing. More preferably, the elastomeric material is comprised of a non-hollow rubber material either molded or extruded to produce a finished elastomeric product without ends. As such, one aspect of the present invention relates to an endless ligation loop wherein the endless loop comprises a non-hollow elastomeric material. As an alternative to using a manufactured preformed elastomeric loop without ends, an elastomeric endless loop may be formed by attaching or connecting the two ends of a straight length of an elastomeric band of rubber or surgical tubing with a clip, wire band, grommet, or other device which prevents the two ends from being separated. In a preferred embodiment, a heavy gauged wire may be used to secure the two ends of the elastomeric band and may further include an end piece capable of being attached to a means for winding or pulling (e.g., hook-like structure).

Figure 12:
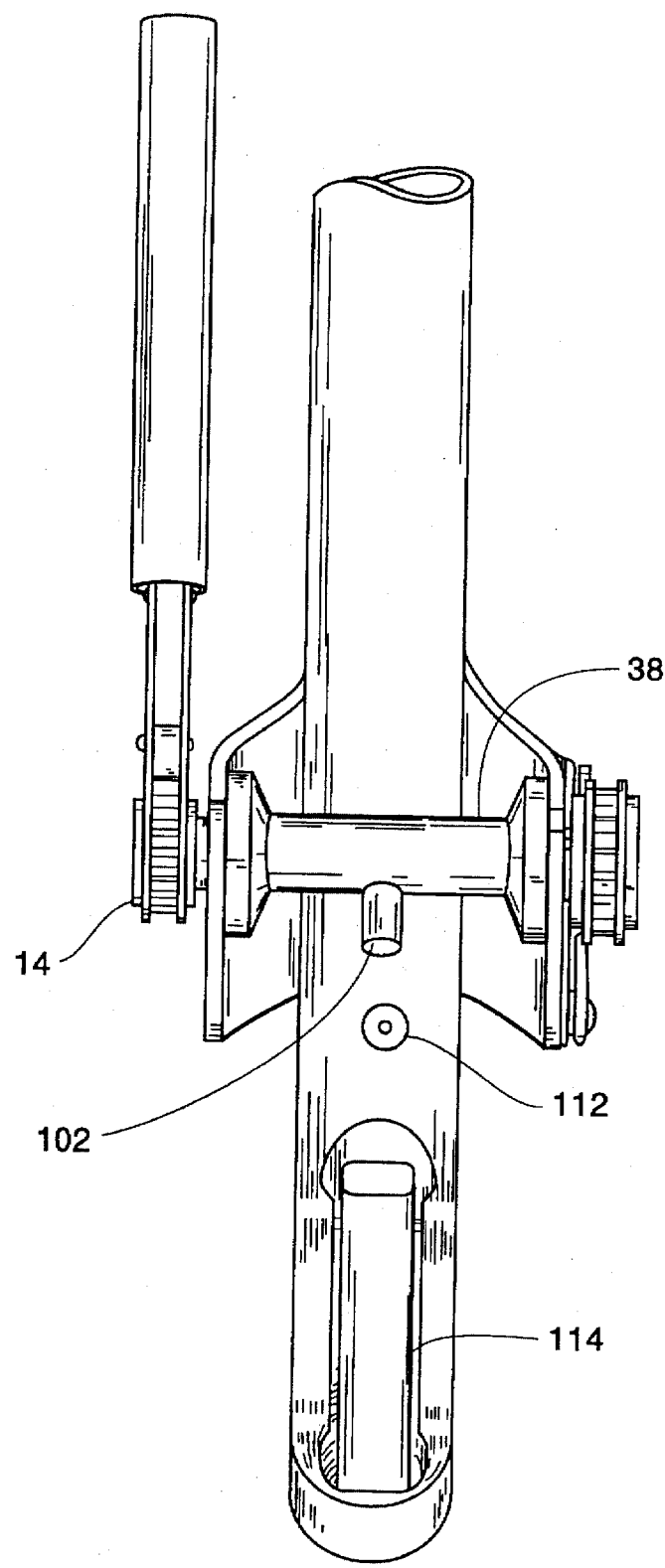
FIG. 12 is a perspective view of the tool showing an integral prong attached to the winding spool.

The endless elastomeric ligature loop 100 is positioned in the receiving end of the tool and connected to an attachment means located on the winding spool 38 (or any suitable pulling means). In a preferred embodiment, a hook-like structure or prong is used to contact the loop and allow the loop to be pulled or wound as shown in FIG. 12. The prong 102 attached to the winding spool 38 may have an integral hook or other type of attachment mechanism to prevent loss of contact with the endless loop during a winding or pulling operation. In a preferred embodiment shown in FIGS. 10 and 12, a hook 104, which attaches to the endless loop is connected to a winding tether 106, which is in turn connected to the winding spool 38. As the winding spool 38 is rotated, the winding tether wraps around the winding spool and begins pulling the endless loop 100 towards the winding spool 38 once sufficient slack is removed from the winding tether 106. The winding tether 106 may be comprised of rope, leather, steel cable, or any other suitable material with a tensile strength sufficient to withstand the forces necessary to operatively tighten the elastomeric loop around the scrotum or other body part of an animal. The endless loop 100 can thus be attached to the winding mechanism quickly without being torn or damaged when tension is placed on the endless loop 100. Furthermore, by utilizing an endless loop in combination with a winding tether 106, significant savings in material costs are realized since the overall length of the endless loop can be decreased. The winding tether 106 and integral hook assembly may be seen in FIG. 10.

Once the endless loop 100 is pulled and/or wound to a desired tension, the loop is constricted so that it is secured around the body part to be ligated. Any suitable means of securing two opposing portions of a loop can be used, including mechanically affixing the loop together or thermally melting the loop material to form a bonding point. Preferably, a grommet 32 is used to secure the endless loop material in a fixed position once sufficient tension is placed on the endless loop to apply adequate pressure around the body part of an animal. The grommet 32 is comprised of metal or any other material which can be permanently deformed. The material preferably has a surface smooth enough to prevent any abrasion when in contact with the elastomeric ligature material, thus preventing tearing of the ligature material. More preferably, the grommet is comprised of rolled flat wire with a length and width sufficient to prevent the ligature material from slipping through the grommet 32 after the grommet 32 is deformed upon the endless loop 100.

Figure 13:
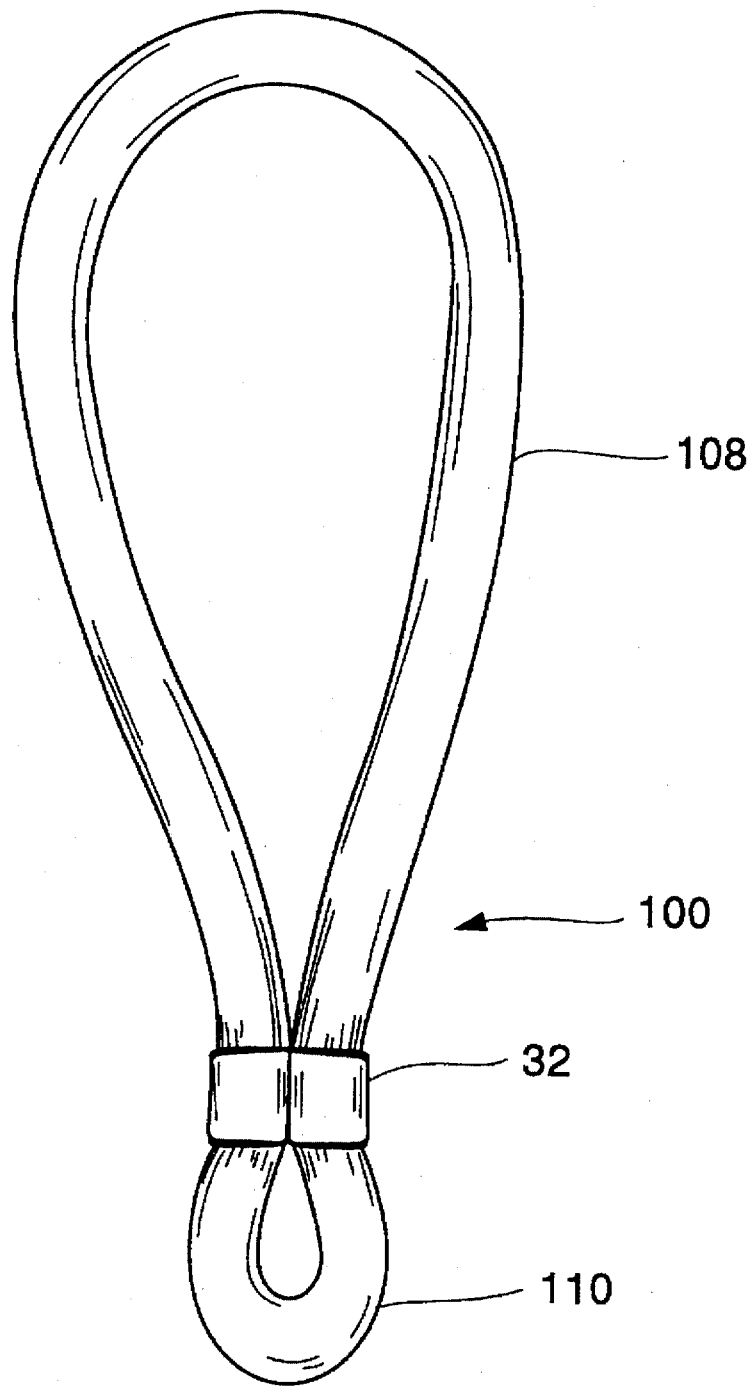
FIG. 13 is a plan view of the endless elastomeric loop and attached grommet.
Figure 14:
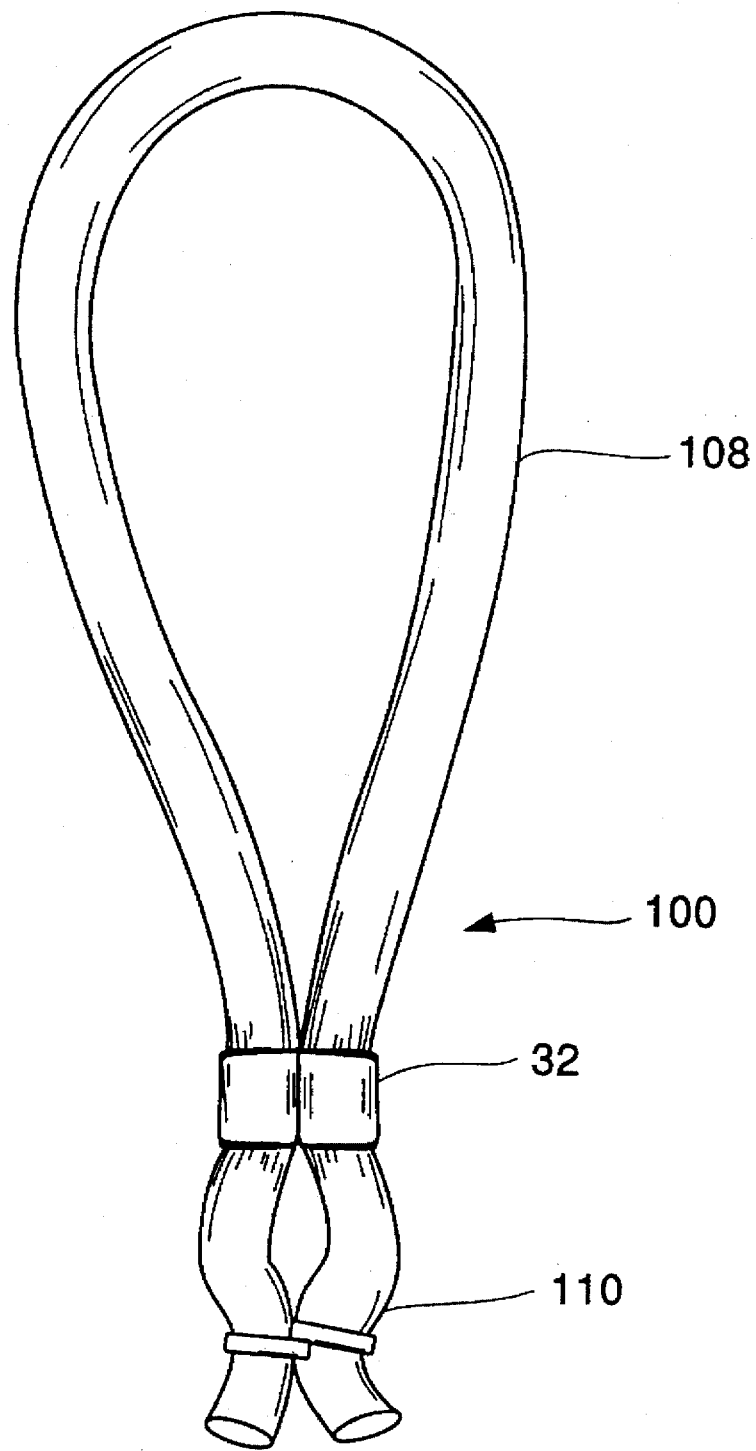
FIG. 14 is a plane view of the endless elastomeric loop with attached grommets, showing attachment of two ends by a wire.
Figure 15:
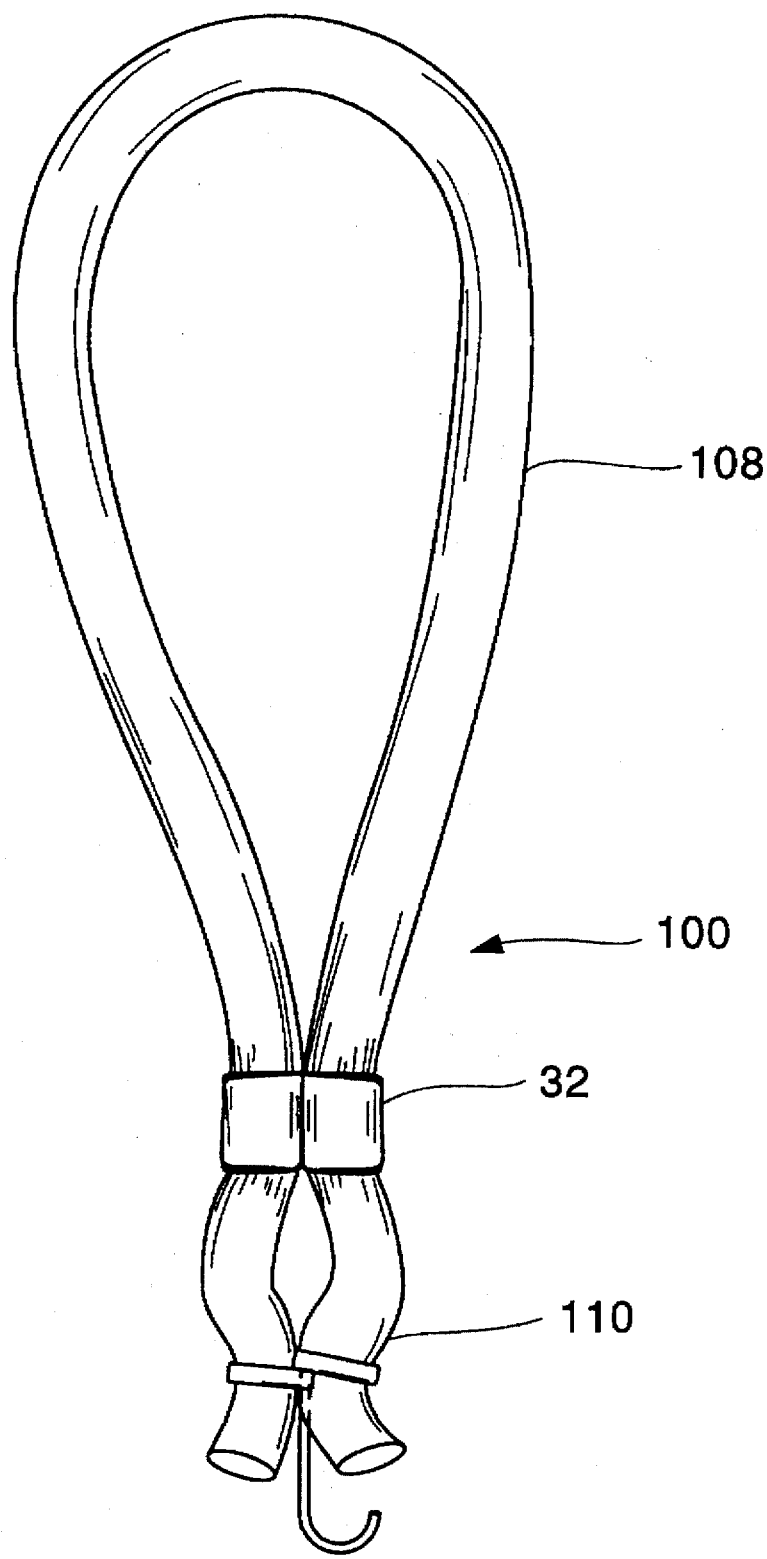
FIG. 15 is a plane view of the endless elastomeric loop and attached grommet showing a wire attaching two ends, such wire having an integral hook connected thereto.

In one embodiment, a grommet 32 is attached to the endless loop 100 prior to actual use, thus assuring that the grommet 32 is attached in a proper manner not likely to damage the endless loop and also preventing the possibility of tightening the loop without first having a grommet in place. Furthermore, by preattaching the grommet 32 to the endless loop, time is saved in the ligation process since the step of feeding the ligature material through the grommet 32 is eliminated. Preferably, and as depicted in FIG. 13, the grommet 32 is attached to the endless loop 100 between a forward end and rearward end of the endless loop, thus forming a forward loop 108 and rearward loop 110, similar to a modified figure-eight or hour-glass configuration. The forward loop 108 extends forward of the receiving end of the tool and the rearward loop 110 extends rearward of the receiving end of the tool. More preferably, the forward loop 108 should be of sufficient circumference to allow it to be easily placed around a selected body part of an animal, such as a scrotum. The rearward loop 110 preferably has a circumference large enough to either allow the attachment of a hook attached to a winding tether 106 (or other pulling means), or to be placed over a prong 102 extending from the winding spool 38. The pre-attached grommet 32 must be loosely attached to the band in a manner that allows the ligature material to slip through the grommet 32 until desired tension on the body part is achieved. At such time, the grommet 32 is deformed to permanently secure the tightened band around the body part.

The receiving end of the tool may have a variety of geometric configurations suitable to receive an equally numerous number of grommet 32 designs. Preferably, the receiving end of the tool has a receptacle 30 with substantially rigid opposing side walls. More preferably, the opposing side walls and opposing top and bottom walls are parallel to one another, whereby the receptacle is substantially square or rectangular in shape. Other embodiments (not shown) can have a receiving end that is open on a top, bottom or side to facilitate easier loading of grommets into the tool.

Figure 11:
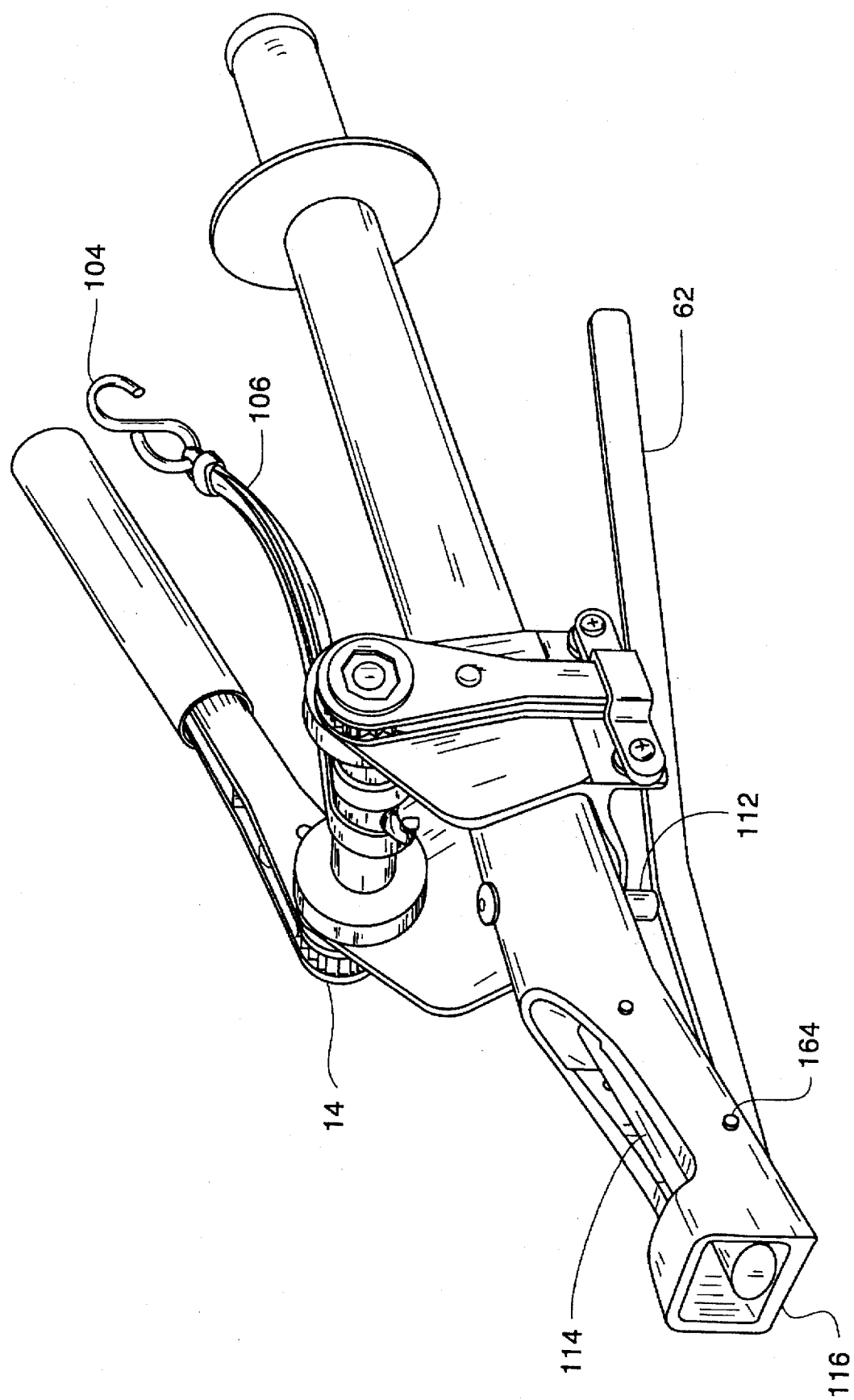
FIG. 11 is a perspective view of the present invention showing the biasing pin, lever, crimping bar and substantially square receptacle located in the receiving end of the tool.

As shown in FIG. 11, the lever 62 pivotally mounted on the body of the tool may be held in a biased position with a biasing pin 112 against the grommet 32 when the grommet is in the receiving end of the tool. The biasing pin 112 may be metallic or any other durable material and extends downward from the tool body. By utilizing a spring, coil or other biasing means, the biasing pin 112 applies constant downward pressure on the lever arm 62, which transfers pressure against the grommet 32 located in the receptacle 30 of the tool. The constant pressure applied by the biasing pin 112 prevents the grommet 32 from inadvertently falling out of or from becoming mispositioned in the receptacle 30 of the tool. Once the endless loop 100 is tightened sufficiently around the body part of the animal, the lever 62 is used to permanently deform the grommet 32 upon the endless loop 100, thus preventing the endless loop 100 from slipping through the grommet. After the grommet 32 is deformed, the lever position is reversed by applying pressure on the rearward portion of the lever in a direction towards the tool body, thus disengaging the tool from the grommet, and thus from the formed endless loop 100. Other means for retaining the grommet in the tool (not shown) include the use of a magnet to reversibly hold a ferrous grommet in place and the use of reversibly flexible structures on the tool and/or the grommet, that act to secure the grommet in a loose fashion to the tool.

Figure 10:
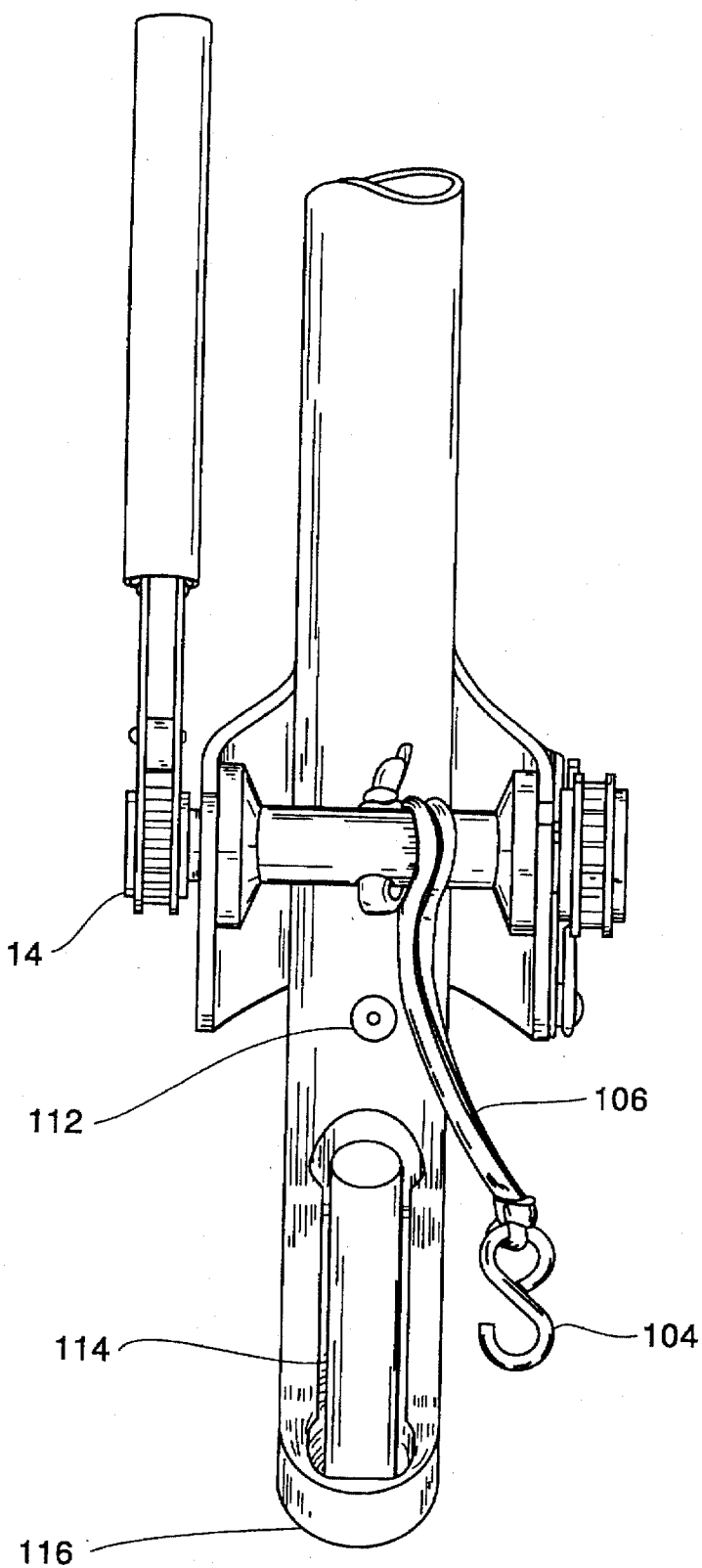
FIG. 10 is a top view of the present invention depicting a winding tether attached to a winding spool and a crimping bar pivotally mounted in the receiving end of the tool.

As illustrated in FIG. 10, the crimping assembly may additionally include a crimping bar 114 located within the receiving end of the tool. Preferably, the crimping bar 114 is pivotally positioned within the receiving end 116 of the tool. The crimping bar 114 is positioned to transfer force from the lever 62 to the grommet 32 when the grommet is positioned in the receptacle 30 in the receiving end 116 of the tool. The crimping bar 114 may be made of steel or other suitable material hard enough to deform the grommet. More preferably, the rearward end of the crimping bar 114 located closest to the winding mechanism of the tool is riveted to the tool body, while the opposite end of the crimping bar 114 is positioned against the grommet 32. As the lever handle is pushed downward and away from the tool body, the upper surface of the lever 62 transfers force to the crimping bar 114, which rotates or pivots upward around the rivet, deforming the grommet. Although the crimping bar 114 used in the present invention has a circular cross-sectional shape, any geometric configuration capable of deforming the grommet may be utilized effectively. The deformation of the grommet against the endless loop 100 thus maintains the endless ligature loop in substantially constant tension around a scrotum or other body part of the animal. Although a grommet is preferably used to secure the endless loop in a fixed position around a body part of an animal, other means for securing the endless loop will be obvious to those skilled in the art. These means include, but are not limited to, the use of plastic or metallic bands or straps, glues, and the application of heat to effectively melt the elastomeric ring in a substantially fixed position.

In a further embodiment of the present invention, means for pulling the endless elastomeric loop 100 rearward to apply tension to the elastomeric loop may be accomplished by rotating the elastomeric loop behind the receiving end of the tool in a direction substantially perpendicular to the longitudinal axis of the tool. This twisting of the loop material around itself (similar to the twisting of a rubber band on a toy propeller airplane) effectively tightens the loop around a body part and eliminates the need for any pulling mechanism. Preferably, the endless elastomeric loop 100 is attached to a sleeve (not shown) which rotates within the tool body and includes an integral hook or pin which attaches to the endless loop. As the sleeve rotates, the endless loop located rearward of the receiving end 116 of the tool rotates, thus shortening the endless loop and applying tension on the portion of the endless loop located forward of the receiving end of the tool. Once sufficient tension is applied to the endless loop 100, a grommet 32 may be attached to the endless loop 100 and deformed at a point adjacent the body part to be ligated.

Another aspect of the present invention involves a method for ligating a body part of an animal, preferably a scrotum. The method involves manually passing a preformed endless loop of ligature material around the body part of the animal. The endless loop is then pulled using various means integral to the ligature tool (e.g. winding mechanisms, pulling mechanisms, etc.) to tighten the loop around the animal's body part. Once the endless loop is sufficiently tightened, the endless loop is secured to maintain adequate pressure around the animal's scrotum. Preferably, the step of securing comprises deforming a grommet around the endless loop, while the pulling of the endless loop is accomplished by winding the endless loop around a winding spool integrally attached to the ligature tool. To improve the efficiency and cost of the method, a winding tether and attached hook may be utilized to reduce the overall length of ligature material necessary. After the grommet is deformed around the endless loop, the excess ligature material not applied around the animal's body part may be removed by cutting the endless loop that is not around the body part with a sharp knife, razor blade or other suitable instrument. Alternatively, the band material can be unwound or otherwise released from the tool, thus eliminating the need to cut the band so as to release it from the tool.

The present invention has a number of advantages over other ligation methods and tools 10. First, the present invention allows a band to be tightened quickly and easily, thereby reducing the time that the animal must be restrained. In addition, the present invention allows the band to be set tightly such that blood flow and systemic support to the body part can be reliably cut off, thereby reducing the likelihood of swelling, infection, prolonged stress to the animal and/or failure of the ligation procedure. Further, because the band is progressively wound about the spool as the loop 20 is tightened, tension forces are spread relatively evenly over the band during the ligation procedure, thereby reducing the likelihood that the band will fail. It is a further advantage of the present invention that larger and stronger elastomeric materials, or relatively inelastic materials, may be used. The present invention also has ease-of-use advantages as band tightening and crimping can be accomplished with relatively little effort. Additionally, the use of a preformed endless elastomeric loop saves time by eliminating the step of attaching loose ends of an elastomeric band to a means for pulling during the ligation operation. Ligature band material costs are also reduced by utilizing a winding tether which is attached to a pulling means, such as the winding spool of the present invention. Further, by preattaching a grommet to the endless loop, proper positioning of the grommet around the endless loop is assured. The possibility of the grommet being jarred from proper positioning in the receiving end of the tool is also minimized by means for holding the grommet in place, for example, by use of the biasing of the lever and crimping bar as previously discussed. Other advantages will be apparent to those skilled in the art.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. An endless ligation loop comprising an endless band of elastomeric ligature material having a deformable grommet slidably attached thereto, said endless loop formed by securely connecting two ends of said ligature material by a wire.

2. The endless ligature loop of claim 1, wherein said deformable grommet has substantially parallel opposing side walls.

3. The endless ligation loop of claim 1, wherein said deformable grommet is attached in a manner so that a forward loop and a rearward loop are formed, said forward loop having a circumference to allow the passage of an animal's body part therethrough.

4. The endless ligation loop of claim 3, wherein said rearward loop is attachable to a means for pulling.

5. The endless ligation loop of claim 1, wherein said endless loop comprises non-hollow elastomeric material.

6. The endless ligature loop of claim 1, wherein said deformable grommet is slidably attached to said loop to allow said loop to travel through said grommet until said grommet is deformed.

7. A method for ligating an animal body part, comprising:
attaching a preformed endless loop of elastomeric material to a ligation tool;
manually passing said loop around a body part of an animal to be ligated;
pulling said loop using said tool to tighten said loop around said body part; and
securing said loop with a grommet so that said loop maintains pressure around said body part of said animal, wherein said step of securing comprises the forming of a grommet around said loop.

8. An endless ligation loop comprising an endless band of elastomeric ligature material having a deformable grommet attached thereto wherein said endless loop is formed by connecting two ends of an endless elastomeric band, said ends connected by a wire, said loop having a circumference to allow passage of an animal's body part therethrough.

9. An endless ligation loop comprising an endless band of elastomeric ligature material having a deformable grommet attached thereto, said endless loop formed by connecting two ends of an endless elastomeric band by a wire, said wire having an integral hook attachable to a means for pulling.

10. An endless ligation loop consisting essentially of an elastomeric ligature material secured together by a connection means, said ligation material having a deformable grommet attached thereto and in sliding engagement therewith, said grommet, upon being deformed, securely fastening said ligature material without significantly damaging said material.

11. A system for castrating an animal, comprising:
a preformed endless loop of elastomeric ligature material, said endless loop having a forward end and a rearward end;
means for receiving said endless loop;
means for pulling said rearward end of said endless loop, said pulling means interconnected to said receiving means; and
means for securing said forward end of said endless loop, wherein the forward end of said endless loop is under tension after being secured, said means for securing interconnected with said receiving means.

12. The system of claim 11, wherein said means for pulling comprises a spool having an axis of rotation generally perpendicular to a longitudinal axis of said means for receiving, said spool having means for connecting said rearward end of said endless loop to said spool.

13. The system of claim 11, wherein said securing means comprises a lever reversibly biased against a grommet.

14. A system for castrating an animal, comprising:
a preformed endless loop of elastomeric ligature material;
an elongated tool body having a forward end and a rearward end, said rearward end having a handle and said forward end having means for receiving said endless loop of elastomeric ligature material;
means for pulling said endless loop towards said rearward end of said tool body, wherein the circumference of said endless loop extending beyond said forward end of said tool body is reduced in size upon pulling of said endless loop, said means for pulling interconnected to said tool body;
a lever pivotally mounted on said tool body for deforming a grommet positioned in said receiving means after said endless loop is pulled rearward; and
means for biasing said lever against said grommet, said means for biasing interconnected with said tool body.

15. The tool of claim 14, wherein said means for receiving comprises a receptacle having substantially rigid opposing side walls for receiving said grommet.

16. The tool of claim 14, further comprising a crimping bar deposed within said means for receiving, said crimping bar oriented to deform a grommet positioned within said receiving means when force is transferred from said lever to said crimping bar.

17. The tool of claim 14, wherein said means for pulling comprises a winding spool integral to said tool, said winding spool having means for attaching a winding tether which is attachable to said endless loop.

18. A method for ligating an animal body part, comprising:
attaching a preformed endless loop of elastomeric material to a ligation tool;
manually passing said loop around a body part of an animal to be ligated;
pulling said loop using said tool to tighten said loop around said body part; and
securing said loop with a grommet so that said loop maintains pressure around said body part of said animal.

19. The method of claim 18, wherein said step of securing comprises deforming a grommet around said loop.

20. The method of claim 18, wherein said step of pulling comprises winding said loop.

21. The method of claim 3, wherein said step of pulling comprises using a motor to tighten said loop around the body part.

22. A method for castrating an animal, comprising:
positioning a preformed endless loop of elastomeric ligature material into a receiving end of a tool, said endless loop having a forward end, a rearward end, and a grommet attached between said forward end and said rearward end; attaching said rearward end of said endless loop to a means for pulling said endless loop;

passing said forward end of said endless loop around the scrotum of an animal;

pulling said rearward end of said endless loop to cause said forward end of said endless loop to constrict around said scrotum of said animal; and securing said forward end of said endless loop to maintain pressure around said scrotum of said animal.

23. A method us set forth in claim 22, wherein said pulling step comprises winding said loop around a spool.

24. A method as set forth in claim 22, wherein said step of attaching comprises attaching a winding tether to said endless loop.

25. A method as set forth in claim 22, wherein said step of securing comprises deforming a grommet onto said endless loop.

26. A method as set forth in claim 22, wherein said preformed endless loop is formed by connecting two ends of an endless elastomeric band.

27. A method as set forth in claim 22, wherein said endless loop comprises non-hollow elastomeric material.

28. A method as set forth in claim 22, wherein said grommet is slidably attached to said loop.

29. A method as set forth in claim 22, wherein said step of pulling comprises using a motor to tighten said loop around the scrotum.

30. A method as set forth in claim 22, wherein said elastomeric ligature material comprises rubber.

31. A method for ligating an animal body part, comprising:

attaching a preformed endless loop of elastomeric material to a ligation tool;

manually passing said loop around a body part of an animal to be ligated;

pulling said loop using said tool to tighten said loop around said body part, wherein said step of pulling comprises using a motor to wind said loop; and securing said loop with a grommet so that said loop maintains pressure around said body part of said animal.

32. A method as set forth in claim 31, wherein said step of pulling comprises engaging said loop with an attachment mechanism to prevent loss of contact between said tool and said loop during said pulling operation.

* * * * *

UNITED STATES PATENT AND TRADEMARK OFFICE
CERTIFICATE OF CORRECTION

PATENT NO.    : 5,681,329
DATED         : October 28, 1997
INVENTOR(S)   : Callicrate It is certified that error appears in the above-identified patent and that said Letters Patent is hereby corrected as shown below:

Column 1,
Line 56, "4,527,179" should read -- 4,572,179 --.

Signed and Sealed this

Twenty-first Day of January, 2003

JAMES E. ROGAN
*Director of the United States Patent and Trademark Office*